United States Patent
Dhaliwal et al.

[11] Patent Number: 5,226,901
[45] Date of Patent: Jul. 13, 1993

[54] COMPOSITE ANESTHETIC ARTICLE AND METHOD OF USE

[76] Inventors: Avtar S. Dhaliwal; Shabir Z. Masih, both of Ste. 43, 408 State of Franklin Rd., Johnson City, Tenn. 37604

[21] Appl. No.: 636,704

[22] Filed: Jan. 2, 1991

Related U.S. Application Data

[60] Continuation-in-part of Ser. No. 179,877, Apr. 11, 1988, abandoned, which is a division of Ser. No. 319,343, Mar. 6, 1989.

[51] Int. Cl.$^5$ .............................................. A61B 19/00
[52] U.S. Cl. .............................................. 604/415
[58] Field of Search .................. 424/663, 686, 43; 604/49, 50, 415

[56] References Cited

U.S. PATENT DOCUMENTS

| | | | |
|---|---|---|---|
| 3,978,212 | 8/1976 | Barna | 424/156 |
| 4,663,166 | 5/1987 | Veech | 424/146 |
| 4,861,592 | 8/1989 | Gottwald et al. | 424/687 |

OTHER PUBLICATIONS

Condouris et al., "Potentiation of the Nerve—Depressant Effect of Local Anesthetics by $CO_2$" Nature, vol. 204, No. 4953, pp. 57-59, 1964.

Martin et al., "Effects of $CO_2$ . . . " Canad. Anaesth. Soc. Jr., vol. 28, No. 3, May 1981, 224-227.

McKay et al., "Sodium Bicarbonate Attenuates Pain . . . " Anesth. Analg. vol. 66, pp. 572-574, 1987.

*Primary Examiner*—C. Fred Rosenbaum
*Assistant Examiner*—Sharon Finkel

[57] ABSTRACT

An aqueous composition for reducing pain at the site of injection of local parenteral anesthetic material, for improving the onset thereof, and for increasing its duration, and a means for preparing and dispensing the same, the composition containing a local parenteral anesthetic which in normal doses gives an acid pH of from about 2.5 to about 6.9, wherein the anesthetic comprises from about 0.5 to about 2.0% by weight of the composition, the composition further containing sufficient $NaHCO_3$ to maintain the pH thereof between about 7.0 and about 7.6, and further containing from about 0.0004 moles of dissolved $CO_2$ per ml of composition up to the saturation level of dissolved $CO_2$ at a $CO_2$ head pressure of up to about 2.5 atmospheres.

9 Claims, 8 Drawing Sheets

COMPOSITE ANESTHETIC ARTICLE AND METHOD OF USE

This application is a continuation-in-part of pending Ser. No. 07/179,877 filed Apr. 11, 1988, now abandoned, and a divisional of pending Ser. No. 07/319,343 filed Mar. 6, 1989, now allowed, in the names of the same inventors and entitled Composite Anesthetic Article and Method of Use.

This invention concerns the modification of materials normally employed as parenteral anesthetics in acidic solution, and particularly concerns a composite article and its method of use which provides in a very convenient manner a buffering system for addition to these acidic materials for reducing certain adverse physiological effects thereof such as burning or stinging generally resulting from injections thereof. The invention also concerns a unique pH buffered, neutral or slightly basic aqueous composition containing a normally acidic parenteral anesthetic, but wherein a pH adjustment from acid to neutral or basic is made completely within a composition article in a hermetically sealed manner substantially immediately prior to injection of the composition.

The acid pH ranging, for example, between 3.5 to 6.5, of intradermal or subcutaneous anesthetic solutions and of most intravenous anesthetic solutions has been implicated as a factor responsible for local irritation at the site of injection, which leads to pain or discomfort during the period of infiltration. The local irritation, redness, tenderness, pain and discomfort near the site of injection and along the course of any proximate vein, appears to be related to the nature of the substances in the parenteral solution and the speed of infiltration. The pH of many commonly used parenteral products such as 0.5-1.0% lidocaine HCl by itself, lidocaine HCl with 1:100,000 Epinephrine, and dextrose infusion, being low (pH 3.5 to 6.5), are known to cause chemical irritation of tissues leading to chemical phlebitis.

As background information, the free esters or amides of local anesthetics such as Lidocaine, Mepivacaine and Bupivacaine are basic substances due to the presence of the amino group. Since free base of such anesthetics are only slightly soluble in water and easily form stable and water soluble salts with mineral and organic acids, the commercial injections of Lidocaine, Mepivacaine and Bupivacaine contain their hydrochloride salts. In the parenteral aqueous solutions, these local anesthetics ionize to give solutions of pH of about 4.0-6.0. In order to decrease the rate and extent of absorption of the local anesthetics into systemic circulation, some of the parenteral solutions contain small amounts of epinephrine. This further reduces the pH of the parenteral solution to about 2.7-3.9.

Table I hereof lists the pH of various commercial local anesthetics, along with the percent of unionized Lidocaine, Mepivacaine and Bupivacaine in the vials as calculated according to equation:

$$pKa - pH = \log c_i/C_u$$

where:
pKa is the negative logarithm of the dissociation constant for the local anesthetic;
pH is the negative logarithm of the hydrogen ion concentration;
$C_i$ is the moles of local anesthetic in the ionized or charged form; and
$C_u$ is the moles of local anesthetic in the uncharged or unionized form.

The data from TABLE I lead to two important conclusions:

(1) the parenteral solutions containing epinephrine HCl are acidic with pH of 2.74-3.1. This acidic pH is responsible for local tissue irritation invoking "Bee Sting-like Pain" at the site of infiltration as well as occasional chemical phlebitis; and (2) the amount of uncharged lipophilic portion of the local anesthetic, which is essential for passive transport into the neuronal axoplasm through the nerve membrane, in most instances, is between 0.0007%-2.44% of the does. Therefore, the rate and extent of diffusion of the uncharged local anesthetic free base is considerably small. This, perhaps, is responsible for the delay of about 2-7 minutes in the onset of analgesia and a waiting period of about 4-12 minutes before surgical procedure can be started.

The advantages therefore of buffered neutral or slightly basic aqueous solutions of such anesthetics are substantial, however, heretofore even though there has been need for a convenient and sterile means for buffering the anesthetic solutions to the correct pH and maintaining such for an appropriate period, such has not been obvious to those conversant in the art and therefore is not available, and little if any real use of this technology has been made. In this regard it is noted that the physical and chemical stability of the free base form of such local anesthetic materials cannot be maintained for more than a few hours after adjustment of pH with, e.g., either sodium hydroxide or sodium bicarbonate, and therefore the commercial injections of Lidocaine, Mepivacaine, and Bupivacaine cannot be buffered, e.g., at pH 7.4 without sacrificing the normal two or more years of shelf life of these materials.

Principal objects therefore of the present invention are: to provide a means and its method of use for making buffer systems such as aqueous bicarbonate solutions readily available to the medical community in a convenient and easy to use unit for the pH adjustment of acidic parenteral anesthetic materials; to provide a means whereby a normally acidic parenteral anesthetic material can be converted to a stable neutral or slightly basic material practically instantly before its use and in an extremely simple manner; and to provide novel, basic buffered parenteral anesthetic compositions having markedly improved analgesic onset and duration.

These and other objects hereinafter appearing have been attained in accordance with the present invention which is defined in one of its principal embodiments as an aqueous composition containing local parenteral anesthetic material, which in normal doses gives an acid pH of from about 2.5 to about 6.9, wherein said anesthetic comprises from about 0.5 to about 2.0% by weight of the system, said composition further containing sufficient $NaHCO_3$ to maintain the pH of said system between about 7.0 and about 7.6, and also containing from about 0.0004 moles of dissolved $CO_2$ per ml of composition to a saturated amount of dissolved $CO_2$.

In another embodiment, the invention is defined as a composite article useful in the buffering of normally acidic parenteral anesthetic material for reducing the adverse physiological effects thereof, said article comprising a vial containing a dilute aqueous system of an acid buffer such as an alkali metal bicarbonate, and a closure cap on said vial hermetically sealing said system therein, said cap having a portion which is readily penetrable by tubular needle means for withdrawing said system from said vial.

In another embodiment, the invention is defined as the method for preparing an aqueous composition containing buffered parenteral anesthetic material, said composition having a pH of from about 7.0 to about 8.5, comprising providing a first vial containing a dilute aqueous solution of an acid buffering system, providing a second vial containing said anesthetic material, each of said vials having a closure cap thereon hermetically sealing the same, and each said cap having a portion which is readily penetrable by the needle of a syringe, inserting said needle through the cap portion of said first vial into said buffering system and withdrawing the same into said syringe, and inserting said needle through the cap portion of said second vial and injecting said system into said second vial to contact said material and buffer the same.

In highly preferred embodiment, the present invention is defined as a composite article useful in the buffering of normally acidic parenteral anesthetic material for reducing the adverse physiological effects thereof, said article comprising a vial having two chambers hermetically isolated from each other by valve means, one of said chambers containing a dilute aqueous system of acid buffer material, the other of said chambers containing acidic parenteral anesthetic material, said valve means being responsive to pressure applied to at least one of said materials to form a fluid connection between said two chambers to allow intermixing of said materials. In this embodiment it is preferred that the valve means comprises a sealing member slidably mounted in the vial and movable under pressure to a position which opens by-pass conduit means for fluid connecting the chambers.

In all of the above embodiments it is preferred that the buffer solution contain $CO_2$, i.e., from about 0.04 to about 0.0004, and preferably from about 0.008 to about 0.002 moles $CO_2$/ml solution. It is most preferable to saturate the buffer solution by bubbling $CO_2$ therethrough until the maximum amount thereof at the particular temperature, e.g., room temperature, is dissolved therein at a $CO_2$ head pressure of up to about 2.5 atmospheres. In this regard, the presence of such quantities of $CO_2$ has been found to significantly enhance the anesthetic action of the present compositions through direct depressant effect of the carbon dioxide itself on neural transmission, through an increase in the fraction of local anesthetic in the nerve axoplasm related to lowering of axoplasm pH through $CO_2$ transfer, and through increased local anesthetic concentration in the axoplasm resulting from diffusion trapping by way of lower intracelluar pH.

Applicants have found that these salutary effects are best achieved where the buffer solution is maintained under adequate $CO_2$ head pressure to force the required $CO_2$ into solution and to maintain this solubility in equilibrium. The molar concentration of $CO_2$ in the pressure head, or the $CO_2$ head pressure per se, for maintaining a predetermined concentration of $CO_2$ in solution at any desirable temperature is readily calculated from the solubility ratio for $CO_2$ of 0.018, for example, at 20° C., according to the Handbook of Chemistry and Physics, and the STP gas laws. It is noted that in achieving the desired forced $CO_2$ solubilization, the volume of the pressure head is immaterial, however, it is highly preferred to maintain a $CO_2$ pressure head volume in the buffer solution vial or syringe chamber such that any exposure of the interior of the vial or chamber to the atmosphere, as may occur by insertion or attachment of a needle, will be at the atmosphere/$CO_2$ interface and not at the buffer surface. In this regard, a slight loss of $CO_2$ in the pressure head will not, on a short term basis, significantly reduce the $CO_2$ concentration in the aqueous buffer system.

In other certain preferred embodiments of the invention:

the solution contains sodium bicarbonate at a concentration of from about 3 to about 20 wt. %, most preferably from about 7.0 to about 8.0 wt. %, and has a pH of from about 7.0 to about 8.5; and the cap is comprised of elastomeric material;

The present invention is useful for buffering a large variety of parenteral anesthetics such as, for example, the aqueous solutions of the following materials: acetamide, 2-(diethylamino)-N-(2, 6-dimethylphenyl)-, monohydrochloride, marketed as Xylocaine; hydroxy compounds such as (−)-3, 4-dihydroxy-d-[(methylamino) methyl] benzyl alcohol, marketed as Epinephrine; procaine HCl; chloroprocaine HCl; tetracaine HCl; pontocaine HCl; propoxycaine HCl; octocaine HCl; prilocaine HCl; mepivacaine HCl; isocaine HCl; bupivacaine HCl; marcaine HCl; and etidocaine HCl.

Typical pharmacological data available in published form on these anesthetics are as follows.

LIDOCAINE HCl
  Indications:
    Infiltration:
      Percutaneous - 0.5% of 1% solution.
      IV regional - 0.5% solution.
    Peripheral nerve block:
      Brachial - 1.5% solution.
      Dental - 2% solution.
      Intercostal or paravertebral - 1% solution.
      Pudendal or paracervical obstetrical (each side) - 1% solution.
    Sympathetic nerve blocks:
      Cervical (stellate ganglion) or lumbar - 1% solution.
    Central neural blocks:
      Epidural -
        Thoracic: 1% solution.
        Lumbar:
          Analgesia - 1% solution.
          Anesthesia - 1.5% or 2% solution.
    Caudal:
      Obstetrical analgesia - 1% solution.
      Surgical anesthesia - 1.5% solution.

-continued

Spinal anesthesia - 5% solution with glucose.
Low spinal or "saddle block" anesthesia: 1.5% solution with dextrose.
Retrobulbar or transtrecheal injection: 4% solution.

| | | | | C.I.* |
|---|---|---|---|---|
| Rx Xylocaine HCl (Astra) | Injection: 0.5% | In 50 ml single and multiple[2] dose vials. | | 7 |
| Rx Lidocaine HCl (Various) | Injection: 1% | In 2 and 5 ml amps, 2, 30 and 50 ml vials, and 5, 10, 20 and 30 ml syringes. | | 2+ |
| Rx Caine-1 (Parnell) | | In 50 ml vials. | | 5 |
| Rx Dilocaine (Hauck) | | In 50 ml vials. | | 6 |
| Rx L-Caine (Century) | | In 50 ml vials. | | 4 |
| Rx Lidoject-1 (Mayrand) | | In 50 ml vials. | | 10 |
| Rx Nervocaine 1% (Keene) | | In 50 ml vials. | | 6 |
| Rx Nulicaine (Kay) | | In 50 ml vials.[2] | | 4 |
| Rx Xylocaine HCl (Astra) | | In 2, 5 and 30 ml amps, 20 & 50 ml multiple dose vials[2] and 30 ml single dose vials. | | 4 |
| Rx Lidocaine HCl (Various) | Injection: 1.5% | In 20 ml amps. | | 27+ |
| Rx Xylocaine HCl (Astra) | | In 20 ml single dose amps & 20 ml single dose vials. | | 36 |

*Cost Index based on cost per ml.
 Price not available from distributor.
[1]With acetone sodium bisulfite.
[2]With methylparaben.

| | | | | |
|---|---|---|---|---|
| Rx Lidocaine HCl (Various) | Injection: 2% | In 2 and 10 ml amps, 2, 5, 30 and 50 ml vials, and 5 and 10 ml syringes. | | 2+ |
| Rx Caine-2 (Parnell) | | In 50 ml vials. | | 5 |
| Rx Dalcaine (Forest) | | In 5 ml vials.[1] | | 52 |
| Rx Dilocaine (Hauck) | | In 50 ml vials.[2] | | 6 |
| Rx Lidoject-2 (Mayrand) | | In 50 ml vials. | | 10 |
| Rx Nervocaine 2% (Keene) | | In 50 ml vials. | | 6 |
| Rx Nulicaine (Kay) | | In 50 ml vials.[3] | | 4 |
| Rx Xylocaine HCl (Astra) | | In 2, 5 and 10 ml amps, 20[2] and 50[2] ml vials, 5 ml syringes and 1.8 ml dental cartridge. | | 7 |
| Rx Xylocaine HCl (Astra) | Injection: 4% | In 5 ml amps. | | 93 |
| Rx Duo-Trach Kit (Astra) | | In 5 ml disp. syringe with laryngotracheal cannula. | | 151 |
| Rx Lidocaine HCl (Various) | Injection: 10% | In 10 ml vials. | | 86+ |
| Rx Lidocaine HCl (Various) | Injection: 20% | In 10 and 20 ml vials and 5 ml syringes. | | 106+ |
| Rx Xylocaine HCl (Astra) | Injection: 0.5% with 1:200,000 epinephrine | In 50 ml vials.[2] | | 7 |
| Rx Xylocaine HCl (Astra) | Injection: 1% with 1:100,000 epinephrine | In 20 and 50 ml vials.[3] | | 10 |
| Rx Xylocaine HCl (Astra) | Injection: 1% with 1:200,000 epinephrine | In 30 ml amps[4] and 30 ml vials.[4] | | 25 |
| Rx Lidocaine HCl (Abbott) | Injection: 1.5% with 1:200,000 epinephrine | In 5 ml amps. | | 89 |
| Xylocaine HCl (Astra) | | In 30 ml amps[4] and 10 and 30 ml single dose vials.[4] | | 26 |
| Rx Octocaine HCl (Novocol) | Injection: 2% with 1:50,000 epinephrine | In 1.8 ml dental cartridge.[5] | | |
| Rx Xylocaine HCl (Astra) | | In 1.8 ml dental cartridge. | | 134 |
| Rx Octocaine HCl (Novocol) | Injection: 2% with 1:100,000 epinephrine | In 1.8 ml dental cartridge.[5] | | |
| Rx Xylocaine HCl (Astra) | | In 20 and 50 ml vials[3] and 1.8 ml dental cartridge. | | 11 |
| Rx Xylocaine HCl (Astra) | Injection: 2% with 1:200,000 epinephrine | In 20 ml amps[4] and 20 ml single dose vials.[4] | | 43 |
| Rx Xylocaine HCl (Astra) | Injection: 1.5% with 7.5% dextrose | In 2 ml amps. | | 357 |
| Rx Xylocaine HCl (Astra) | Injection: 5% with 7.5% glucose | In 2 ml amps. | | 321 |

*Cost Index based on cost per ml.
 Price not available from distributor.
[1]Preservative free.
[2]With methylparaben.
[3]With methylparaben and sodium metabisulfite.
[4]With sodium metabisulfite.
[5]With sodium bisulfite.

LOCAL ANESTHETICS, INJECTABLE

Complete prescribing information for these products begins on page 691.

BUPIVACAINE HCl

Indications:
    Local infiltration: 0.25% solution.
    Lumbar epidural: 0.25%, 0.5% and 0.75% solutions (0.75% nonobstetrical).
    Subarachnoid block: 0.75% solution.
    Caudal block: 0.25% and 0.5% solutions.
    Peripheral nerve block: 0.25% and 0.5% solutions.

-continued

| | | | C.I.* |
|---|---|---|---|
| | Retrobulbar block: 0.75% solution. | | |
| | Sympathetic block: 0.25% solution. | | |
| | Dental block: 0.5% solution with epinephrine. | | |
| Rx Bupivacaine HCl (Abbott) | Injection: 0.25% | In 20 ml amps and 50 ml syringes. | 45 |
| Rx Marcaine HCl (Winthrop Pharm.) | | In 50 ml amps and 10, 30 and 50[1] ml vials. | 21 |
| Rx Sensorcaine (Astra) | | In 30 ml amps and 30 and 50[1] ml vials. | 19 |
| Rx Bupivacaine HCl (Abbott) | Injection: 0.5% | In 20 ml amps and 30 ml syringes. | 48 |
| Rx Marcaine HCl (Winthrop Pharm.) | | In 30 ml amps and 10, 30 and 50[1] ml vials. | 29 |
| Rx Sensorcaine (Astra) | | In 30 ml amps and 10, 30 and 50[1] ml vials. | 19 |
| Rx Bupivacaine HCl (Abbott) | Injection: 0.75% | In 20 ml amps and 20 ml syringes. | 41 |
| Rx Marcaine HCl (Winthrop Pharm.) | | In 30 ml amps and 10 and 30 ml vials. | 34 |
| Rx Marcaine Spinal (Winthrop Pharm.) | | In 2 ml single dose amps.[2] | 192 |
| Rx Sensorcaine (Astra) | | In 30 ml amps. | 22 |
| Rx Marcaine HCl (Winthrop Pharm.) | Injection: 0.25% with 1:200,000 epinephrine | In 50 ml amps[3] and 10,[3] 30[3] and 50[4] ml vials. | 21 |
| | 0.5% with 1:200,000 epinephrine | In 3 and 30 ml amps[3] and 10,[3] 30[3] and 50[3] ml vials. | 29 |
| | 0.75% with 1:200,000 epinephrine | In 30 ml amps.[3] | 30 |
| Rx Marcaine with Epinephrine (Cook-Waite) | Injection: 0.5% with 1:200,000 epinephrine | In 1.8 ml dental cartridges.[3] | |
| Rx Sensorcaine (Astra) | Injection: 0.5% with 1:200,000 epinephrine | In 5 and 30 ml amps[4] and 30 ml vials.[5] | 22 |
| | 0.75% with 1:200,000 epinephrine | In 30 ml amps[4] and 30 ml vials.[5] | 21 |

ETIDOCAINE HCl

Indications:
    Peripheral nerve block, central nerve block or lumbar peridural: 1% solution.
    Intra-abdominal or pelvic surgery, lower limb surgery or caesarean section: 1% or 1.5% solution.
    Caudal: 1% solution.
    Maxillary infiltration or inferior alveolar nerve block: 1.5% solution.

| | | | C.I.* |
|---|---|---|---|
| Rx Duranest HCl (Astra) | Injection: 1% | In 30 ml single dose vials. | 48 |
| | 1% with 1:200,000 epinephrine | In 30 ml single dose vials.[3] | 52 |
| | 1.5% with 1:200,000 epinephrine | In 20 ml amps.[5] | 82 |

*Cost Index based on cost per ml.
  Price not available from distributor.
[1]With methylparaben.
[2]With 0.25% dextrose.
[3]With sodium metabisulfite and EDTA.
[4]With sodium metabisulfite, EDTA and methylparaben.
[5]With sodium metabisulfite.

LOCAL ANESTHETICS, INJECTABLE

Complete prescribing information for these products begins on page 691.

PRILOCAINE HCl

Indications:
    For local anesthesia by nerve block or infiltration in dental procedures: 4% solution.

| | | | C.I.* |
|---|---|---|---|
| Rx Citanest HCl (Astra) | Injection, Plain: 4% | In 1.8 ml dental cartridge. | 17 |
| | Injection, Forte: 4% with 1:200,000 epinephrine | In 1.8 ml dental cartridge.[1] | 17 |

MEPIVACAINE HCl

Indications:
    Nerve block (eg, cervical, brachial, intercostal, pudendal): 1% or 2% solution.
    Transvaginal block (paracervical plus pudendal): 1% solution.
    Paracervical block in obstetrics: 1% solution.
    Caudal and epidural block: 1%, 1.5% or 2% solution.
    Infiltration: 1% solution.
    Therapeutic block: 1% or 2% solution.
    Dental procedures (infiltration or nerve block): 3% solution or 2% solution with levonordefrin.

| | | | C.I.* |
|---|---|---|---|
| Rx Carbocaine (Winthrop Pharm.) | Injection: | | |
| | 1% | In 30 ml vials and 50 ml[2] vials. | 21 |
| | 1.5% | In 30 ml vials. | 28 |
| | 2% | In 20 ml vials and 50 ml[2] vials | 35 |
| Rx Carbocaine (Cook-Waite) | Injection: 3% | In 1.8 ml dental cartridge. | |

-continued

| | | | |
|---|---|---|---|
| Rx Isocaine HCl (Novocol) | | In 1.8 ml dental cartridge. | |
| Rx Polocaine (Astra) | | In 1.8 ml dental cartridge. | 18 |
| Rx Carbocaine with Neo-Cobefrin (Cook-Waite) | Injection: 2% with 1:20,000 levonordefrin | In 1.8 ml dental cartridge.[3] | |
| Rx Isocaine HCl (Novocol) | | In 1.8 ml dental cartridge.[4] | |

*Cost Index based on cost per ml.
Price not available from distributor.
[1]With sodium metabisulfite.
[2]With methylparaben.
[3]With acetone sodium bisulfite.
[4]With sodium bisulfite.

LOCAL ANESTHETICS, INJECTABLE

Complete prescribing information for these products begins on page 691.

PROCAINE HCl, INJECTABLE

Indications:
  Infiltration anesthesia: 0.25% to 0.5% solution.
  Peripheral nerve block: 0.5% to 2% solution.
  Spinal anesthesia: 10% solution.
  Dilution instructions: To prepare 60 ml of a 0.5% solution (5 mg/ml), dilute 30 ml of the 1% solution with 30 ml sterile distilled water. To prepare 60 ml of a 0.25% solution (2.5 mg/ml), dilute 15 ml of the 1% solution with 45 ml sterile distilled water. Add 0.5 to 1 ml of epinephrine 1:1000 per 100 ml anesthetic solution for vasoconstrictive effect (1:200,000 to 1:100,000).

| | | | C.I.* |
|---|---|---|---|
| Rx Procaine HCl (Various) | Injection: 1% | In 2 ml amps and 30 and 100 ml vials. | 2+ |
| Rx Novocain (Winthrop Pharm.) | | In 2 and 6 ml amps and 30 ml vials. | 4 |
| Rx Procaine HCl (Various) | Injection: 2% | In 30 and 100 ml vials. | 2+ |
| Rx Novocain (Winthrop Pharm.) | | In 30 ml vials. | 28 |
| Rx Novocain (Winthropo Pharm.) | Injection: 10% | In 2 ml amps.[1] | 208 |

CHLOROPROCAINE HCl

Indications:
  Infiltration and peripheral nerve block: 1% to 2% solution.
    Mandibular - 2% solution.
    Infraorbital - 2% solution.
    Brachial Plexus - 2% solution.
    Digital (without epinephrine) - 1% solution.
    Pudendal block - 2% solution.
    Paracervical block - 1% solution.
  Infiltration, peripheral and central nerve block, including caudal and epidural block: 2% or 3% solution (without preservatives).

| | | | C.I.* |
|---|---|---|---|
| Rx Nesacaine (Astra) | Injection:[2] 1% | In 30 ml vials. | 36 |
| | 2% (Not for epidural or caudal block.) | In 30 ml vials. | 36 |
| Rx Nesacaine-MPF (Astra) | Injection:[3,4] 2% | In 30 ml vials. | 39 |
| | 3% | In 30 ml vials. | 41 |

TETRACAINE HCl

Indications:
  Spinal anesthesia (high, median, low and saddle blocks): 0.2% to 0.3% solution.
  Spinal anesthesia, prolonged (2 to 3 hours): 1% solution.
  Store under refrigeration.

| | | | C.I.* |
|---|---|---|---|
| Rx Pontocaine HCl (Winthrop Pharm.) | Injection: 1% | In 2 ml amps.[1] | 158 |
| | 0.2% with 6% dextrose | In 2 ml amps. | 155 |
| | 0.3% with 6% dextrose | In 5 ml amps. | 79 |
| | Powder for reconstitution | In 20 mg Niphanoid (instantly soluble) amps | 32 |

*Cost Index based on cost per ml.
[1]With acetone sodium bisulfite.
[2]With methylparaben and EDTA.
[3]Preservative free.
[4]With EDTA.

TABLE I pH OF SOME PARENTERAL LOCAL ANESTHETIC SOLUTIONS AND EXTENT OF IONIZATION AT THE pH OF THE SOLUTION

| PARENTERAL SOLUTION | pH | pka of Local Anesthetic | % Ionized | % Uncharged |
|---|---|---|---|---|
| 1% Lidocaine Hcl | 6.3 | 7.9 | 97.56 | 2.44 |
| 1% Lidocaine Hcl with 1:100,000 Epinephrine Hydrochloride | 2.74 | 7.9 | 99.999 | 0.0007 |
| 2% Lidocaine Hcl | 7.02 | 7.9 | 88.36 | 11.64 |
| 2% Lidocaine Hcl with 1:100,000 Epinephrine Hydrochloride | 3.89 | 7.9 | 99.99 | 0.0098 |
| 0.5% Lidocaine | 5.96 | 7.9 | 98.86 | 1.13 |
| 0.5% Lidocaine Hcl with 1:200,000 Epinephrine Hydrochloride | 3.79 | 7.9 | 99.99 | 0.0078 |
| 0.25% Bupivacaine Hcl | 6.2 | 8.1 | 88.82 | 11.18 |
| 0.25% Bupivacaine Hcl with 1:200,000 Epinephrine Hcl | 3.91 | 8.1 | 99.994 | 0.0065 |
| 2% Mepivacaine Hcl | 5.56 | 7.6 | 99.09 | 0.90 |
| 2% Mepivacaine Hcl with 1:200,000 Epinephrine | 3.505 | 7.6 | 99.99 | 0.0079 |

TABLE II

EFFECT OF NEUTRA-CAINE ® ON THE IONIZATION AND pH OF LOCAL ANESTHETICS JUST PRIOR TO INFILTRATION

| CASE | PARENTERAL SOLUTION | AMOUNT (ml) | pH AFTER MIXING | ADMIXTURE % UNCHARGED | % IONIZED |
|---|---|---|---|---|---|
| I | 1% Lidocaine Hcl<br>NEUTRA-CAINE ® | 20.0<br>4.0 | 7.59 | 32.88 | 67.12 |
| II | 1% Lidocaine Hcl &<br>1:100,000 Epinephrine<br>NEUTRA-CAINE ® | 20.0<br>4.0 | 7.51 | 28.95 | 71.05 |
| III | 0.5% Lidocaine Hcl<br>NEUTRA-CAINE ® | 20.0<br>4.0 | 7.90 | 50.00 | 50.00 |
| IV | 0.5% Lidocaine Hcl &<br>1:200,000 Epinephrine<br>NEUTRA-CAINE ® | 20.0<br>4.0 | 7.54 | 30.39 | 69.61 |
| V | 2% Lidocaine Hcl &<br>1:100,000 Epinephrine<br>NEUTRA-CAINE ® | 20.0<br>4.0 | 7.39 | 23.61 | 76.39 |
| VI | 0.25% Bupivacaine Hcl<br>0.9% Sodium Chloride<br>NEUTRA-CAINE ® | 10.0<br>15.0<br>1.0 | 7.90 | 38.69 | 61.31 |
| VII | 0.25% Bupivacaine Hcl &<br>1:200,000 Ephinephrine<br>0.9% Sodium Chloride<br>NEUTRA-CAINE ® | 10.0<br>15.00<br>1.0 | 7.78 | 32.37 | 67.63 |
| VIII | 2% Mepivacaine Hcl<br>NEUTRA-CAINE ® | 20.0<br>4.0 | 7.3 | 33.39 | 66.61 |
| IX | 2% Mepivacaine Hcl &<br>1:200,000 Epinephrine<br>NEUTRA-CAINE ® | 20.0<br>4.0 | 7.1 | 24.03 | 75.97 |

NOTE:
The amount of NEUTRA-CAINE ® added must be controlled, according to the knowledge of the solubility of free base in the medium. If excess buffer is added which shifts the pH to more alkaline side the solution becomes turbid and is rendered unsuitable for infiltration.

In preparing the buffering system, particularly the bicarbonate system, carbon dioxide is used to adjust the pH toward a lower value. In accordance with the present invention, the present vials or syringe are hermetically sealed, preferably to retain the carbon dioxide in solution, as aforesaid under pressure. In this regard, and as one aspect of the present invention as noted above, Applicants have found that when such predetermined amounts of carbon dioxide are dissolved in the buffer solution and predetermined amounts of carbon dioxide gas are provided to maintain head pressure in the vial or syringe, the pH is maintained in equilibrium which improves the onset and duration of action, e.g., of the solubilized Lidocaine, Mepivacaine and Bupivacaine, when the buffer material is mixed with them in prescribed proportion, just prior to infiltration. It is noted, in this regard that many commercial solutions of sodium bicarbonate either do not contain carbon dioxide or contain only very small amounts thereof typically through generation from chemical reactions in-situ between sodium bicarbonate and acids such as citric acid. Also, the vials used for such materials have not been available as single dose vials which are necessary for eliminating contamination and the carrying of infection. Furthermore, the labeling of these commercial products only permit intravenous use for the treatment of metabolic acidosis as associated with cardiac arrest. No therapeutic indications as the present invention makes obvious are claimed by the marketers nor are such indications as yet, being heretofore unobvious, approved by FDA.

An in-vitro experiment published by professors Conouris, G. A. and Shakalis, A., entitled Potentiation of the nerve depressant effect of local anesthetics by carbon dioxide. Nature, 204:57-59, 1964 using rat peripheral nerve preparation was designed to show the effect of carbon dioxide on conduction of nerve impulses. The nerve preparation was exposed to solution in Tyrode (standard electrolyte material used in physiological investigations) without carbon dioxide, to solution of Tyrode with carbon dioxide, and to solution of lidocaine hydrochloride in Tyrode containing varying amount of carbon dioxide. A supramaximal electrical stimulation was applied to the nerve exposed in the different solutions and the resulting spike, as a measure of conduction of nerve impulses, was recorded. The degree of reduction in spike height provided a means to determine the extent of blocking action by various treatments to the nerve. FIG. 4 clearly demonstrates that carbon dioxide potentiates the pharmacological action of lidocaine hydrochloride by a factor of 5-10.

It may now be clear, why certain prior available solutions of sodium bicarbonate did not improve the pharmacological effect of local anesthetics to the same degree as the present material. The principal reason is that these prior solutions of sodium bicarbonate did not contain carbon dioxide, or the amount thereof in the solution was insufficient. The commercial preparations which incorporate carbon dioxide into the vial by way of chemical reaction between sodium bicarbonate and a weak organic acid such as citric acid are not only deficient in the amount of carbon dioxide but also in the amount of sodium bicarbonate. The present material, on the other hand, contains the full required amount of sodium bicarbonate as well as an adequate amount of dissolved carbon dioxide, in addition to adequate free carbon dioxide to provide desired head $CO_2$ pressure for maintaining proper pH within the vial or syringe. The compositions and quantities therefore for preferred vial or syringe loadings for the buffer and the mixed components of the present invention, as exemplified by lidocaine hydrochloride anesthetic and sodium bicarbonate buffer are as follows:

| | | | |
|---|---|---|---|
| Anesthetic Component | lidocaine hydrochloride | 50 | mg. |
| | deionized water | 5 | ml |
| Buffer Component | sodium bicarbonate | 75 | mg. |
| | deionized water | 1.0 | ml |
| | dissolved $CO_2$ | 0.02 | moles |
| | head pressure $CO_2$ | 21.58 | psi |
| Mixed Components | lidocaine hydrochloride | 50 | mg. |
| | sodium bicarbonate | 6 | mg. |
| | dissolved $CO_2$ | 0.02 | moles |
| | head pressure $CO_2$ | ~21 | psi |
| | deionized water | 6 | ml |

Table II hereof shows the pH of the anesthetic solutions after mixing with a prescribed amount of the present buffer solution, also referred to herein as NEUTRA-CAINE. In contrast with the data in Table I, the data in Table II shows a substantially large amount of uncharged free base of the local anesthetic. This observation explains, on the basis of physicochemical principles, the role of NEUTRA-CAINE in the overall improvement of the performance of local anesthetics, while providing patient comfort and compliance. In this regard, FIG. 5 schematically illustrates the mechanism of transport of the local anesthetic free bases from the site of infiltration into the neuronal axoplasm. Data in Table I and Table II support the pH-Partition hypothesis of drug absorption. It is suggested in this regard (USP DI, Drug Information for health care provider Vol. I, pp. 142-169, 1986: Pub. United States Pharmacopeial Convention, Inc., Rockville, Md.) that the local anesthetics reversibly stabilize the neuronal membrane and decrease its permeability to sodium ion. The decrease in the permeability of sodium ion inhibits the depolarization phase of the neuronal membrane and thereby stops the propagation of action potential and blocks the initiation and conduction of sensory and motor nerve impulses (see FIGS. 6 and 4).

In order to demonstrate that a pH of b 7.2 is more effective for nerve block from lidocaine than the pH of 9.2, an isolated sciatic nerve of a frog was mounted on sucrose gap apparatus (Strobel, George E. and Bianchi, C. Paul. The effects of pH gradients on the action of procaine and lidocaine in intact and desheathed sciatic nerves., J. Phammacol. Exp. Ter. 172:1-17, 1970.). The nerve was equilibrated in ringer solution and the proximal end of the nerve was stimulated by an electrical impulse generator. The action potentials were recorded during equilibration in ringer solution and subsequently in ringer solution containing lidocaine. Action potentials were also recorded while the pH of the fluid bathing the nerve was changed from 9.2 to 7.2 and back to 9.2 FIG. 6 shows that the rate of decrease in action potential from exposure of the nerve to lidocaine solution at pH 9.2 was much slower than the rate of decrease at pH 7.2. This observation is consistent with the scheme of FIG. 5 and the data in Tables I and II. The action potential from lidocaine solution at pH 9.2 was slower, perhaps, due to the increased concentration of free base which exceeded the solubility of the base in the medium. The practical implication of this observation is that inadequate and improper amount of sodium bicarbonate mixed with the local anesthetics, without calculation of the degree of ionization and without knowledge of the solubility of the base can lead to poor performance of the mixture. Data from a well controlled study design supports the recommended amount of NEUTRA-CAINE necessary to improve the efficacy without impeding the solubility and physical instability of the free base and insures the reliability of the performance of NEUTRA-CAINE in reducing the pain associated with infiltration of local anesthetics, and in improving the onset and duration of action. Of course, the rate and extent of absorption of local anesthetics, like any other drug, depends on the route and site of administration, the degree of vascularity at the site of infiltration, the pH of the parenteral solution, and the presence or absence of vasoconstrictor in the parenteral solution.

As shown in Table II, considerably higher proportions of uncharged lipid-soluble local anesthetic are available for absorption into systemic circulation or into the neuronal axoplasm at pH above 7.0. From a safety view point, it is necessary to show that the plasma levels of lidocaine, mepivacaine, and bupivacaine, do not reach above 3.0 microgram per milliliter to avoid neurological and cardiovascular complications.

Lidocaine HCl, lidocaine HCl with epinephrine, lidocaine HCl mixed with sodium bicarbonate, and lidocaine HCl and epinephrine mixed with sodium bicarbonate, were administered, epidurally, to five subjects in five different groups in a parallel design (Martin, R., Lamarche, Y., and Tetreault, L., Effects of carbon dioxide and epinephrine on serum levels of lidocaine after epidural anesthesia., Canad. Anaesth. Soc. J., 28:224–227, 1981.). Sequential blood samples were collected over two hour post dosing and analyzed for lidocaine level in the serum. FIG. 7 shows that in no case the serum lidocaine levels exceeded 2.5 mcg/ml which is lower than the reported level of 3.0 mcg/ml within 5 minutes following the intravenous injection of lidocaine (Snider, S. M. and Way, E. L., The kinetics of transfer of lidocaine across the human placenta., Anesthesiology 29:944–950.). Therefore it can be concluded that NEUTRA-CAINE is not likely to induce toxic blood level of lidocaine following an intradermal or subcutaneous injection.

The local anesthetics used for infiltrative local anesthesia cause patient discomfort in form of "Bee Sting-like" pain due to local pH related tissue irritation. Although, a slight reduction in painful discomfort can be achieved through the use of 25 gauge needle and a very slow rate of infiltration, the time constraints on physician and the case of a fearfully agitated and ailing patient, particularly children in the emergency departments, demands a simple alternate procedure. Experimental evidences indicate that NEUTRA-CAINE provides that simple painless alternative procedure.

Two independent randomized, prospective double-blind studies (Christoph, R. A., Buchanan, L., Begalia, K., and Schwartz, S., Pain reduction in local anesthetic administration through pH buffering., Ann. Emer. Med 17:117–120, 1988.), evaluated the effect of sodium bicarbonate buffered lidocaine, in 25 and 24 human subjects, respectively, on the reduction of infiltrative pain from local anesthetics. FIG. 8, illustrates that mean pain score was significantly lower for lidocaine injection buffered with sodium bicarbonate. Many subjects reported that the local anesthetic mixed with sodium bicarbonate was painless. Over a 61% reduction in mean pain score is reported (McKay, W., Morris, R., and Mushlin, P., Sodium bicarbonate attenuates pain on skin infiltration with lidocaine, with or without epinephrine, Anesth. Analg. 66:572–574, 1987) from the use of sodium bicarbonate buffer.

The preceding data show that NEUTRA-CAINE helps in the reduction of pain from infiltration of local anesthetics by adjusting the pH of the fluids. It has also been shown that more uncharged free base of the local anesthetic is available for absorption into the neuronal axoplasm at pH close to 7.2 and that the conduction of electrical impulses through isolated peripheral nerve of frog is blocked much more rapidly by lidocaine in the presence of buffer. Improved clinical efficacy of lidocaine in the presence of buffer has been studied in 148 adult patients who underwent either cesarean section, or postpartum tubal ligation, or lower extremity orthopedic procedures, or lithotripic treatment (DiFazio, C. A., Carron, H., Grosslight, K. R., Moscicki, J. C., Bolding, W. R., and John, R. A., Anesth. Analg. 65:760–764, 1986.), using a double blind parallel study design. The patients received, by epidural injection, either lidocaine with epinephrine and saline at pH 4.6, or lidocaine solution with epinephrine and sodium bicarbonate buffer like NEUTRA-CAINE at pH 7.15 or lidocaine with epinephrine at pH 4.55. After the administration of the appropriate treatment the time for the onset of analgesia and the waiting time required before starting surgery was noted. FIGS. 9 and 10, summarize the results of the studies which demonstrates that the time of onset of analgesia was reduced from 7 minutes to 2 minutes in the treatment where the pH was adjusted to 7.2. The waiting time for surgery was also reduced from 12 minutes to 5 minutes.

The invention will be further understood from the following description and drawing wherein.

Figure 4:
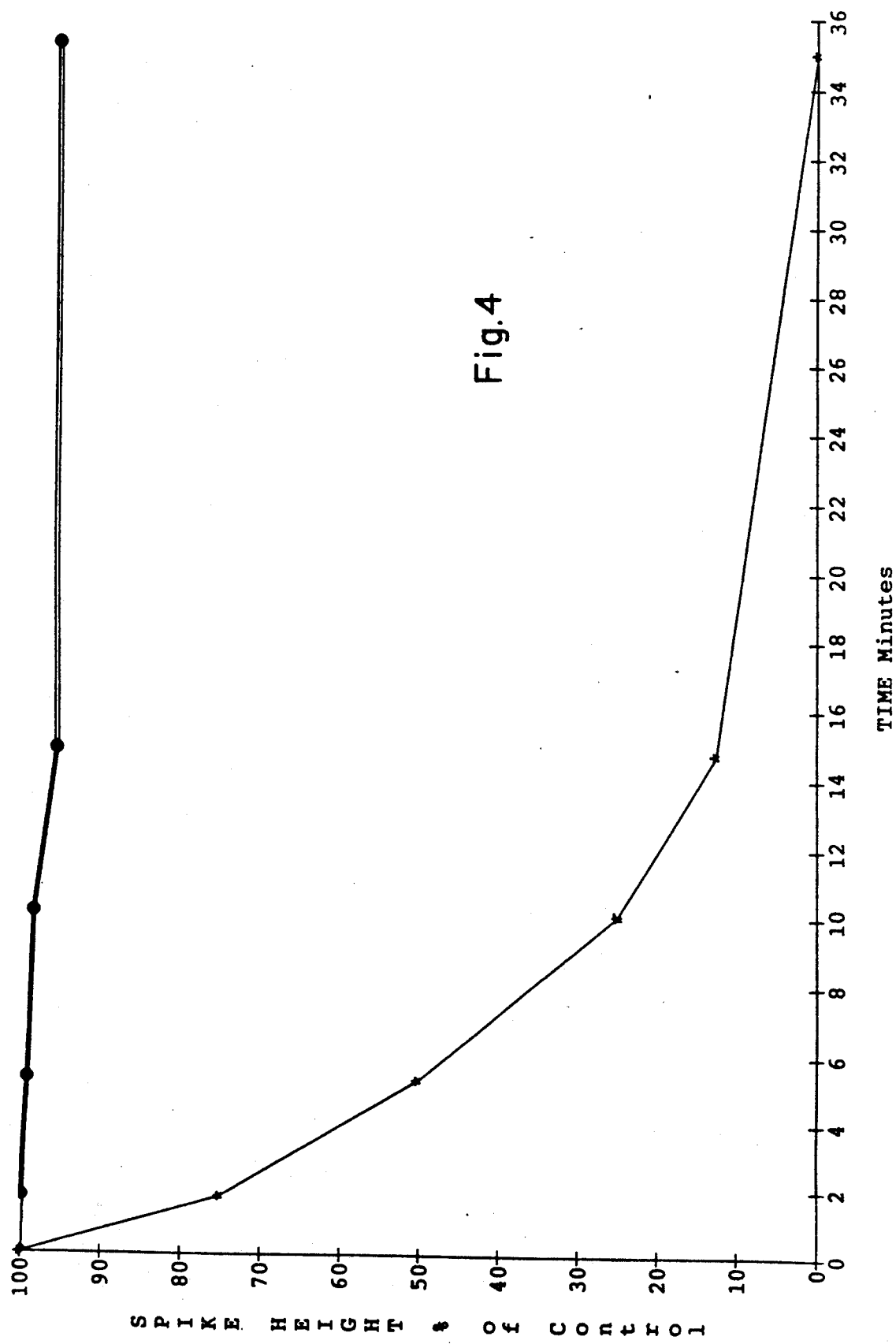
Figure 5:
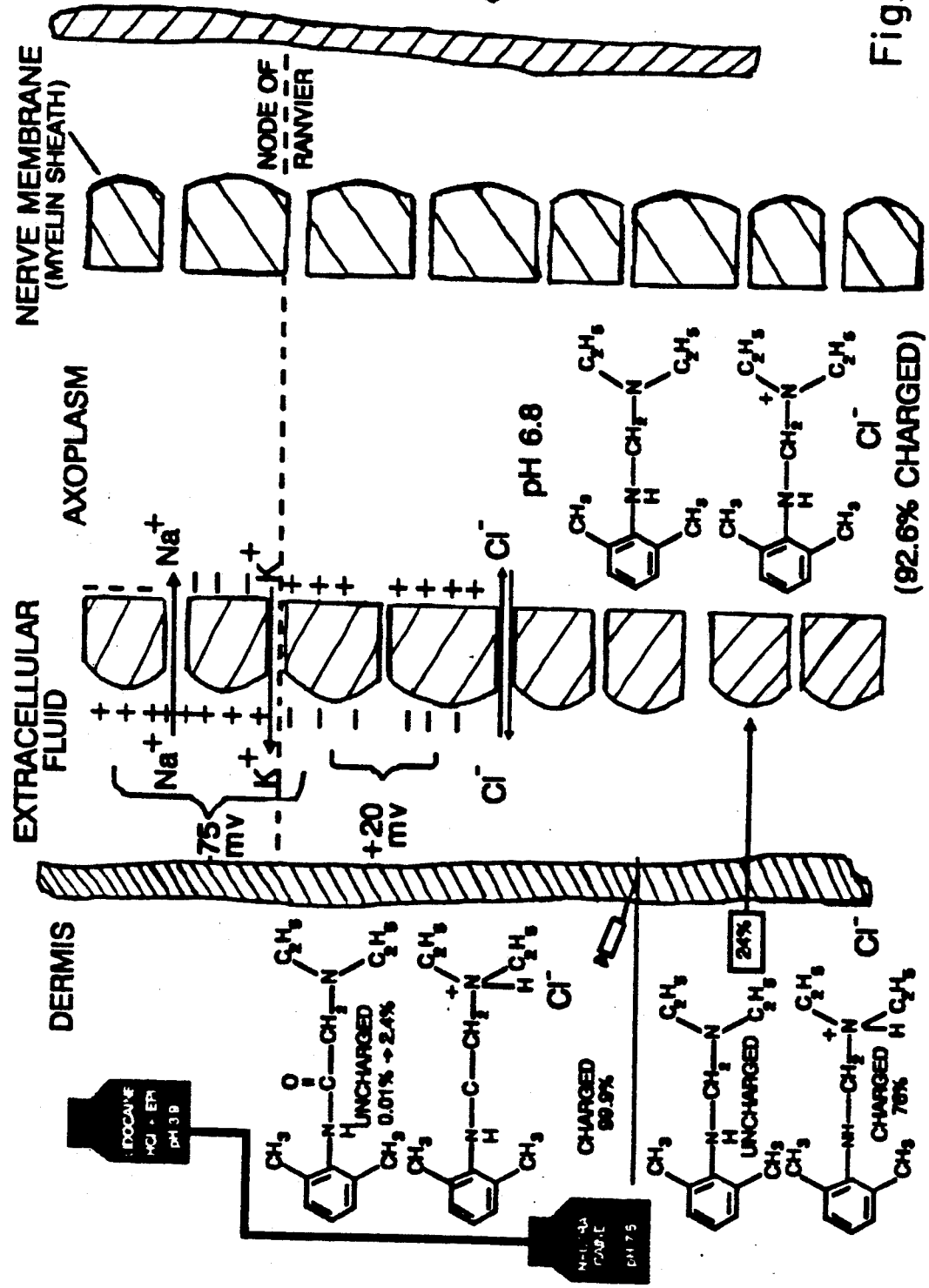
Figure 6:
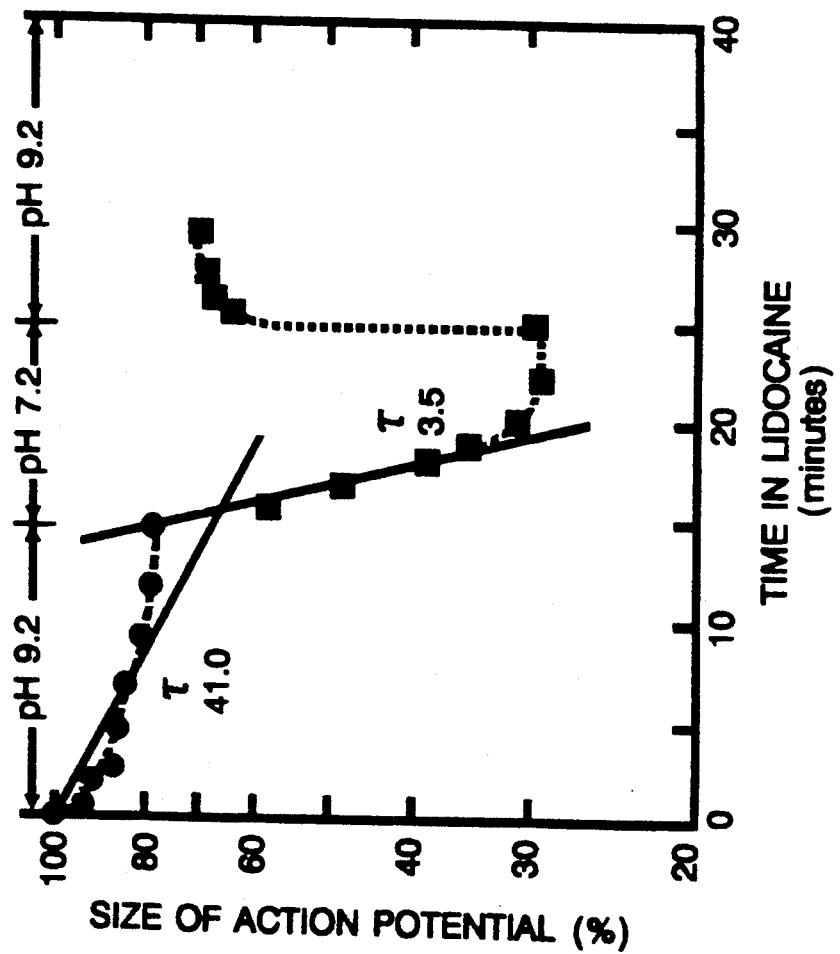
Figure 7:
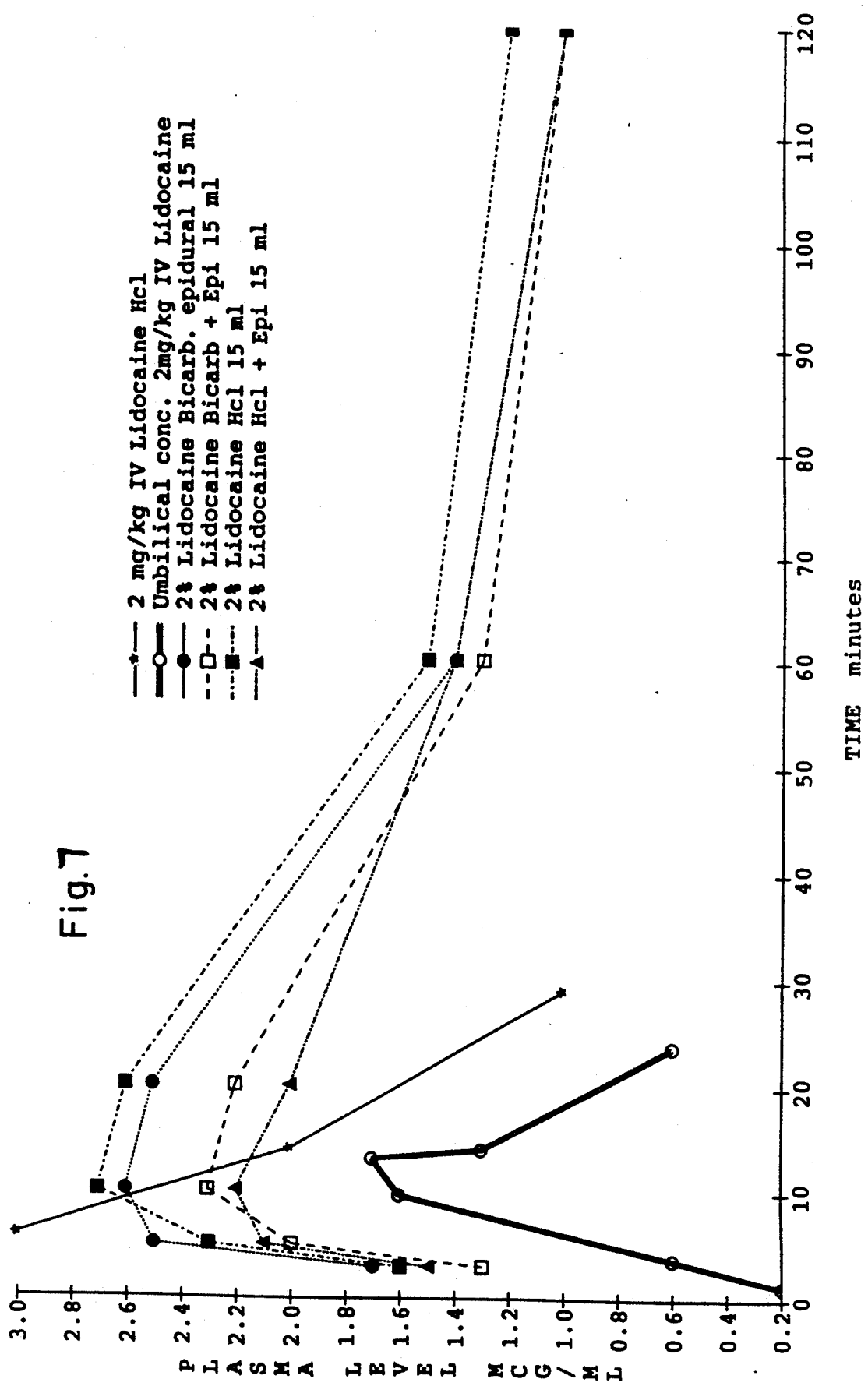
Figure 8:
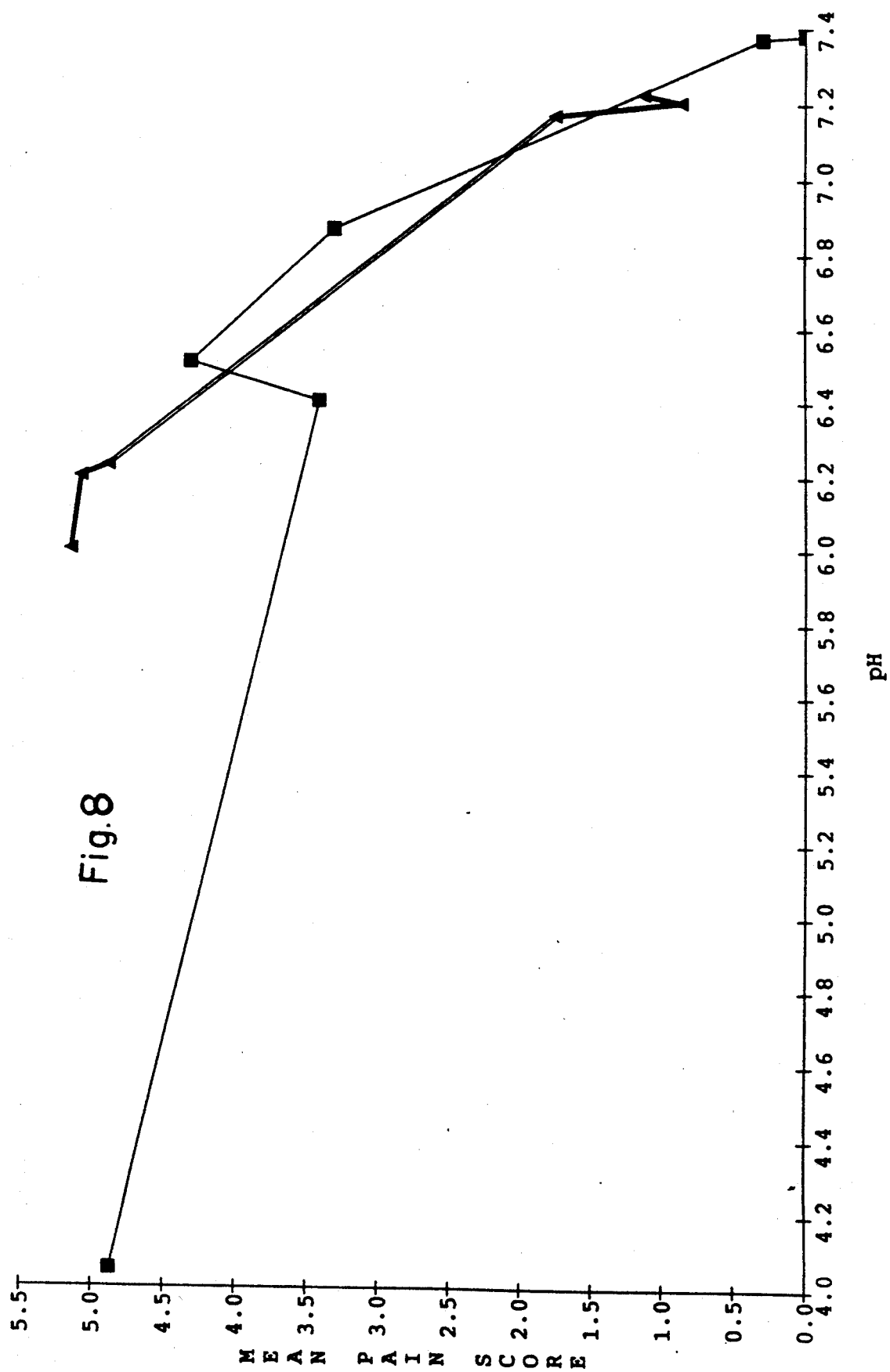
Figure 9:
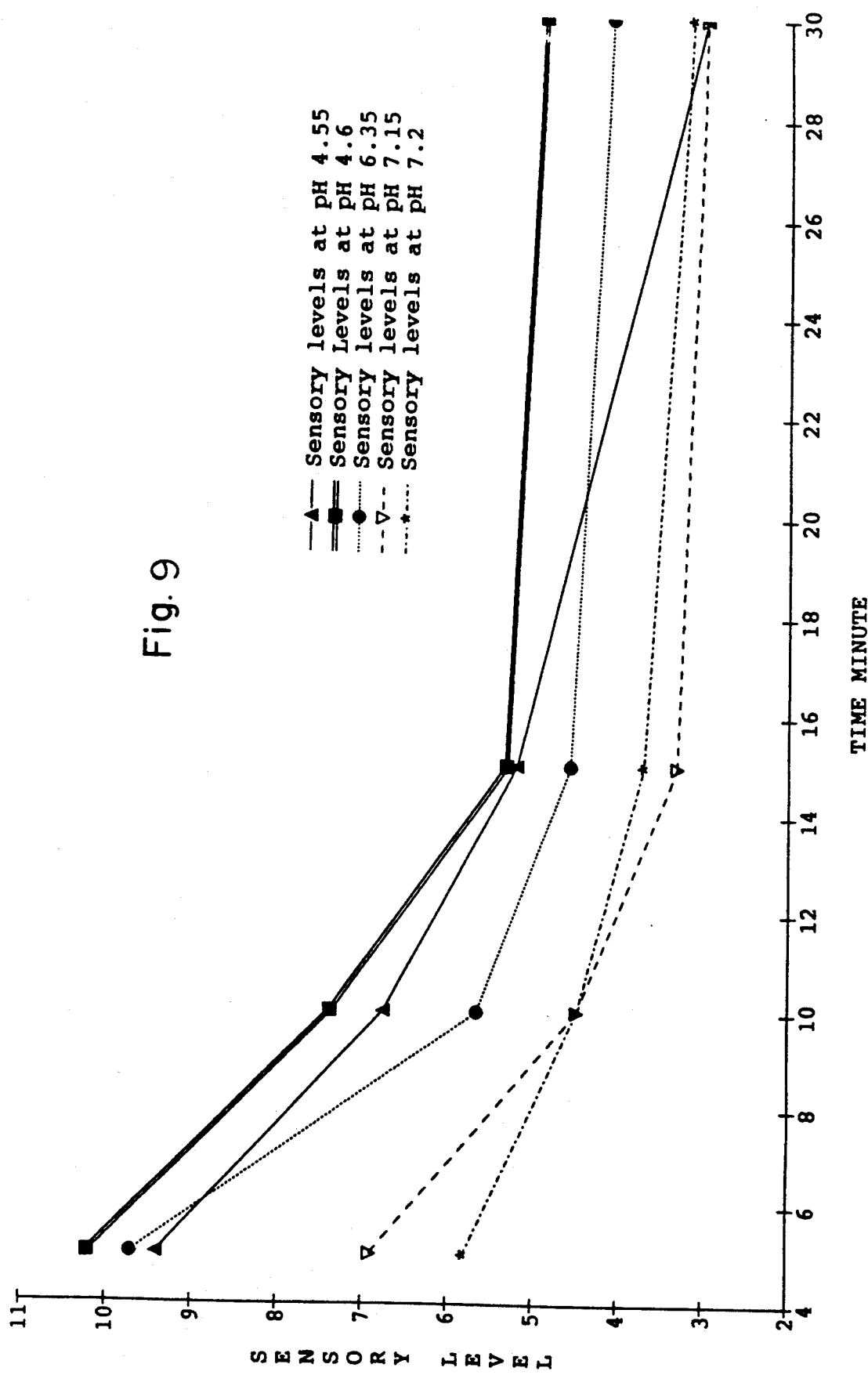
Figure 10:
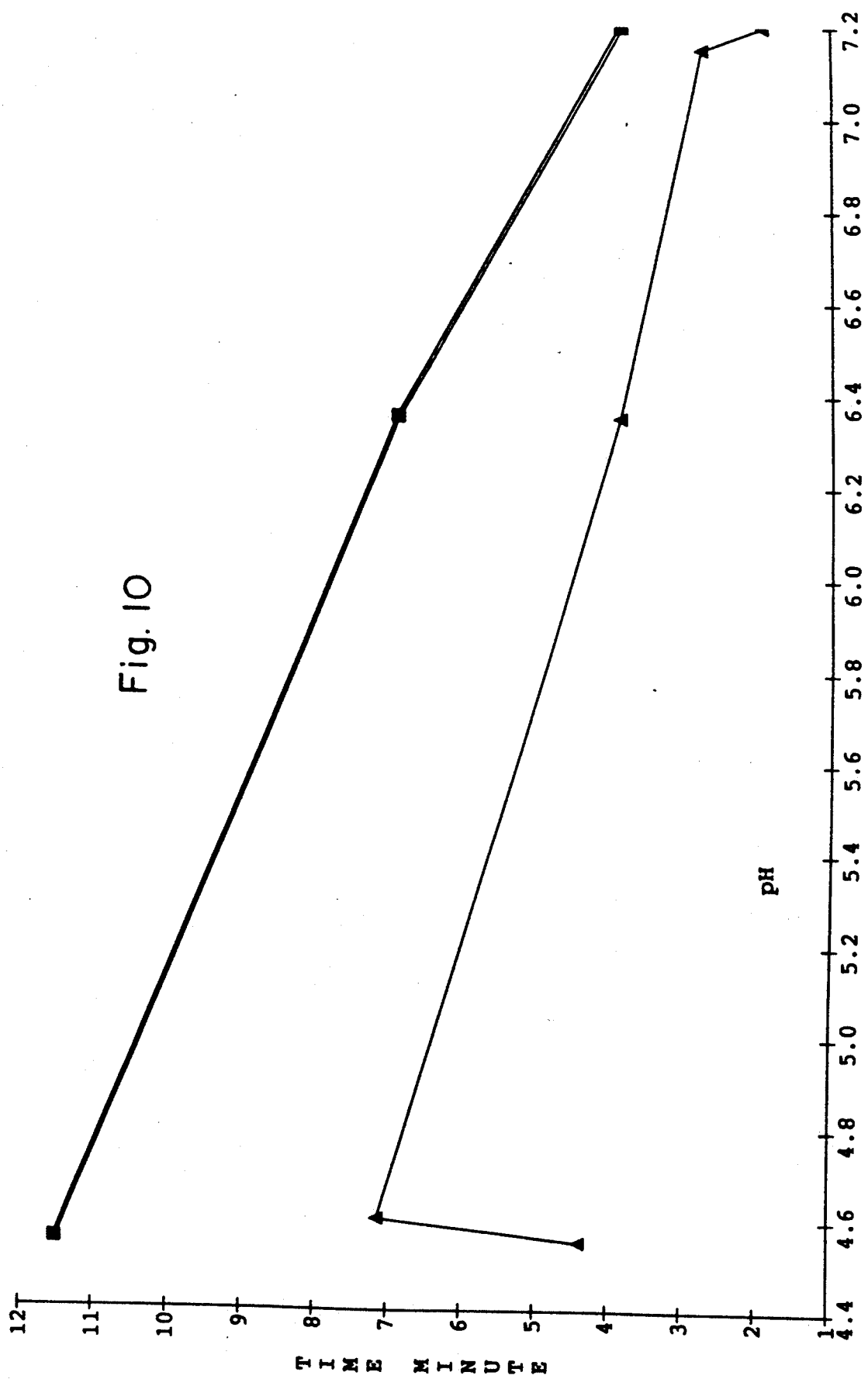

FIG. 4 shows in graph form the effect of carbon dioxide on the spike potential of frogs peripheral nerve following electrical stimulation in carbon dioxide treated lidocaine wherein, on the graph, the asterisks are points on the curve for the nerve submerged in lidocaine solution treated with $CO_2$, and the dots are points on the curve for the nerve submerged in control solution without $CO_2$ treatment;

FIG. 5 is a schematic of the mechanism of transport of the local anesthetic free base from the site of infiltration into the neuronal axoplasm;

FIG. 6 shows in graph form the contrasting effects of pH on block by lidocaine in the myelinated fibers of desheathed frog sciatic nerve trunk. Local anesthetics, 0.50 mM in Ringer's, were substituted for Ringer's at time zero. The pH was 9.2 for the dot points and 7.2 for the square points;

FIG. 7 shows in graph form the plasma level of lidocaine following various treatments;

FIG. 8 shows in graph form the mean pain scores as a function of pH of lidocaine solution in two independent studies wherein the black square points graph represents parallel double-blind in 24 subjects (McKay et al, Anesth. Analg. 66:572–5, 1987), and the black triangle points graph represents parallel double-blind study I (Christoph et al, Ann. Em. Med. 17:117–120, 1988);

FIG. 9 shows in graph form the sensory level as a function of time following lidocaine injection of varying pH; and FIG. 10 shows in graph form the time for onset of anesthesia and waiting period for surgery as a function of pH of lidocaine injection, wherein the black triangular points represent the time for onset of anesthesia (DiFazio et al., Anesth. Analg. 65:760–764), and the black square points represent the time waiting for surgery.

Figure 1:
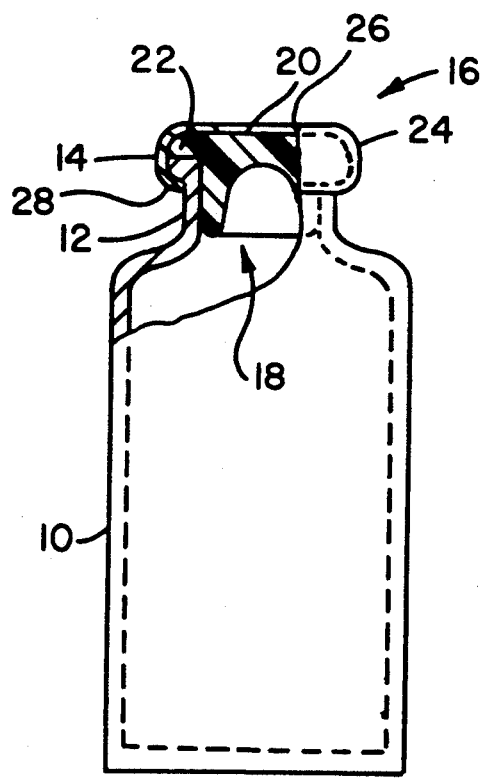
FIG. 1 is a partial longitudinal cross-sectional view of an exemplary vial (2× scale) useful in the present invention.

Referring to FIG. 1 of the drawing, the vial consists of a body 10, preferably circular, of glass, ceramic, plastic such as polyester, polycarbonate, polyurethane, polyolefin, or polyamide, or elastomer such as neoprene, polybutadiene, or the like, or metal such as stainless steel or aluminum, having a neck 12 provided with a lip 14. A cap generally designated 16 comprising a stopper 18 having a web portion 20 and a rim portion 22, is hermetically sealed against the lip 14 of the bottle body by a metal locking ring 24 of annular configuration having an annular opening 26, in its top providing access to web portion 20 for inserting a syringe or hypodermic needle therethrough and into the bicarbonate or other buffer solution. Ring 24 is clamped into compression under lip 14 and over rim portion 22 by a metal forming operation which curls a shoulder 28 of the ring underneath lip 14. Stopper 18 is manufactured such that at least its center web portion 20 is readily penetrable by the aforesaid syringe or hypodermic needle for withdrawing the buffer solution from the vial body. The composition of 18 therefore is preferably an elastomeric material such as butyl rubber, neoprene, polybutadiene or the like. The vial is typically filled about ⅔ with the buffer solution before the cap is locked into place. In a typical method of using the present composite article, the precalculated required amount of the buffer solution is drawn into the syringe or hypodermic body through the needle thereof inserted through the stopper web portion, and then injected into the acidic aqueous anesthetic solution, again preferably through the cap web portion of its container or vial of similar construction. The two solutions are then thoroughly mixed by gentle agitation and the buffered anesthetic is then ready for use. The proportions of buffering system and anesthetic material will, of course, vary depending on the materials used and the pH desired, however, a typical buffered anesthetic solution will contain 1.0 ml of the present 7.5 wt. % sodium bicarbonate solution and 5.0 ml of a 0.5–1.0 wt. % aqueous solution of lidocaine hydrochloride.

Figure 3:
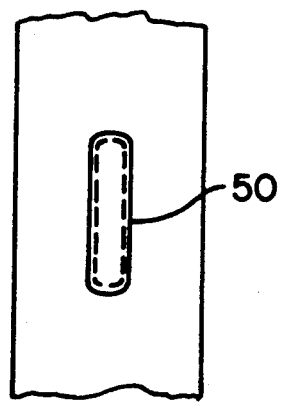
FIG. 3 is a view of the by-pass area of the syringe taken in the direction of the arrow "3" in FIG. 2.
Figure 2:
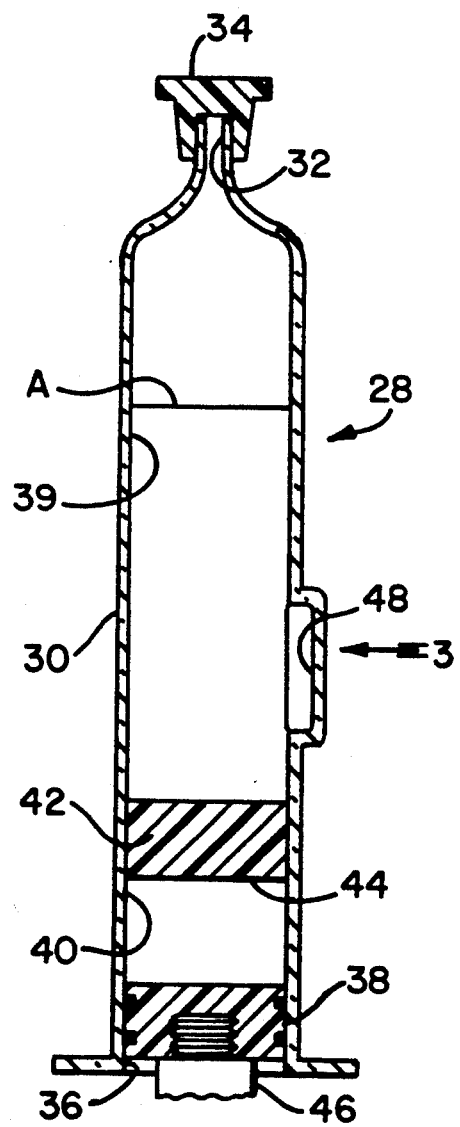
FIG. 2 is a cross-sectional view of a syringe preferred for the present invention.

Referring to FIGS. 2 and 3 of the drawing, the preferred syringe generally designated 28 comprises body 30 of glass or tough plastic material having a needle attaching nib 32 at its proximal end normally sealed by a cap 34, and a filler opening 36 at its distal end normally sealed by a piston 38. Body 30 is divided into two chambers, 39 and 40 which normally are hermetically separated by a valve member 42, which member is sealingly slidable upwardly in the body in response to pressure being applied to its surface 44 by movement of plunger 46 and the attached piston 38 further into the body. A by-pass conduit 48 is provided by an outward protrusion 50 in the body wall and is normally inoperative as shown.

In a typical operation of the syringe, with the valve member 42 in place, approximately as shown, the chamber 39 is filled with buffer solution, preferably containing $CO_2$ and sealed by cap 34 and piston 42. The syringe is made ready for use by forcing the piston 38 further into the body to force and position the valve member 42 in a substantially longitudinally centralized position with respect to the by-pass conduit 48 such that the solution in chamber 40 will be forced through the by-pass conduit and into the buffer solution. Upon release of force on piston 38, the valve will move below the by-pass and trap the admixed solutions in chamber 39 where they can be agitated, e.g., by gently shaking to intimately mix them for use.

As alternatives to the alkali metal bicarbonates, other buffering materials can be employed either alone or in combination with the bicarbonates, and include, for example, chemically equivalent amounts of the alkali metal acetates, borates, phosphates and phthalates, which of course, must be used only on a selective basis as determined by the particular use being made of the anesthetic, the tissue involved and the chemical sensitivity of the particular patient.

The invention has been described in detail with particular reference to preferred embodiments thereof, but it will be understood that variations and modifications will be effected within the spirit and scope of the invention.

I claim:

1. The method for preparing an aqueous solution of a buffered parenteral anesthetic, said solution having a pH of from about 7.0 to about 8.5 and ready for immediate injection into the human body at the time of medical procedure, said method comprising providing a first vial containing a dilute aqueous acid buffering system containing essentially electrolyte-free water and sodium bicarbonate, providing a second vial containing a parenteral anesthetic having in non-buffered form a pH of below 7.0, each of said vials having a closure cap thereon hermetically sealing the same, and each said cap having a portion which is readily penetrable by the needle of a syringe, inserting said needle through said cap portion of said first vial into said buffering system and withdrawing the same into said syringe, and inserting said needle through said cap portion of said second vial and injecting said buffering system into said second vial to contact said anesthetic and buffer the same to a pH of above 7.0.

2. The method of claim 1 wherein the amount of buffering system withdrawn from said first vial and injected into said second vial is predetermined to give a concentration of said anesthetic in said solution of from about 0.5 to about 2.0% by weight thereof.

3. The method of claim 2 wherein said syringe needle is retained in said second vial and the buffered solution of anesthetic is withdrawn by said syringe when needed and injected into the patient directly from said syringe.

4. The method of claim 1 wherein said non-buffered anesthetic has a pH of from about 3.5 to about 6.5, the dissolved solids of said buffering system consists essentially of sodium bicarbonate at a concentration of from about 3 to about 20 wt. %, and said system contains at least about 0.0004 moles of dissolved $CO_2$ per ml of said system, and said system has a pH of from about 7.0 to about 8.5.

5. The method of claim 4 wherein said cap is comprised of elastomeric material.

6. The method of claim 5 wherein the concentration of the sodium bicarbonate is about 7.0 to about 8.0 wt. %.

7. The method of claim 5 wherein the anesthetic material is an aqueous solution of one or a mixture of lidocaine hydrochloride or (−)-3, 4-dihydroxy- -[(methylamino) methyl] benzyl alcohol.

8. The method of claim 5 wherein the anesthetic material is an aqueous solution of one or a mixture of lidocaine hydrochloride or (−)-3, 4-dihydroxy- -[(methylamino) methyl] benzyl alcohol.

9. The method of claim 5 wherein the concentration of the sodium bicarbonate is about 7.5 wt. %.

* * * * *